United States Patent
Takei

(10) Patent No.: US 11,896,292 B2
(45) Date of Patent: Feb. 13, 2024

(54) MEDICAL DEVICE AND TREATMENT SYSTEM

(71) Applicant: Olympus Corporation, Hachioji (JP)

(72) Inventor: Yusuke Takei, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 1089 days.

(21) Appl. No.: 16/722,334

(22) Filed: Dec. 20, 2019

(65) Prior Publication Data

US 2020/0121386 A1    Apr. 23, 2020

Related U.S. Application Data

(63) Continuation of application No. PCT/JP2017/024345, filed on Jul. 3, 2017.

(51) Int. Cl.
*A61B 18/14* (2006.01)
*A61B 17/00* (2006.01)
(Continued)

(52) U.S. Cl.
CPC ............ *A61B 18/1445* (2013.01); *A61B 2017/00398* (2013.01); *A61B 2018/0063* (2013.01); *A61B 2018/00601* (2013.01); *A61B 2018/126* (2013.01); *A61B 2018/1226* (2013.01); *A61B 2018/1266* (2013.01)

(58) Field of Classification Search
CPC ............ A61B 18/1445; A61B 2017/00398
See application file for complete search history.

(56) References Cited

U.S. PATENT DOCUMENTS

| 4,691,461 A | 9/1987 | Behlert |
| 5,307,660 A | 5/1994 | Stoutenburg |

(Continued)

FOREIGN PATENT DOCUMENTS

| JP | H06-184588 A | 7/1994 |
| JP | H09-253088 A | 9/1997 |

(Continued)

OTHER PUBLICATIONS

Sep. 26, 2017 International Search Report issued in International Patent Application No. PCT/JP2017/024345.

(Continued)

*Primary Examiner* — Linda C Dvorak
*Assistant Examiner* — Ryan T Clark
(74) *Attorney, Agent, or Firm* — Oliff PLC

(57) ABSTRACT

A medical device comprises a housing and a sheath having opposed proximal and distal ends and being attached from the proximal end to the housing. An end effector is attached to the distal end portion of the sheath. The end effector includes a pair of grasping jaws capable of be openable and closable with respect to one another. A movable shaft includes a distal end that being connected at to the end effector and configured to be movable with respect to the sheath so as to cause the paired grasping jaws to be opened or closed with respect to one another. A movable handle is configured to pivot with respect to the housing and having an input position where an operation is inputted so as to cause the handle to pivot. The movable shaft is changeable in an initial state before the operation is inputted at the input position.

20 Claims, 10 Drawing Sheets

(51) Int. Cl.
    *A61B 18/00*    (2006.01)
    *A61B 18/12*    (2006.01)

(56) References Cited

U.S. PATENT DOCUMENTS

| | | |
|---|---|---|
| 2007/0282371 A1 | 12/2007 | Lee et al. |
| 2012/0116379 A1* | 5/2012 | Yates .................... A61B 34/25 606/33 |
| 2013/0053831 A1* | 2/2013 | Johnson ............... A61B 18/085 606/1 |
| 2013/0304115 A1 | 11/2013 | Miyamoto |
| 2014/0336698 A1* | 11/2014 | Boudreaux ........ A61B 18/1447 606/206 |
| 2015/0335347 A1 | 11/2015 | Hirai et al. |
| 2016/0317215 A1* | 11/2016 | Worrell .............. A61B 18/1445 |

FOREIGN PATENT DOCUMENTS

| | | |
|---|---|---|
| JP | 2009-539472 A | 11/2009 |
| WO | 2013/021850 A1 | 2/2013 |

OTHER PUBLICATIONS

Jan. 7, 2020 International Preliminary Report on Patentability issued in International Patent Application No. PCT/JP2017/024345.

\* cited by examiner

MEDICAL DEVICE AND TREATMENT SYSTEM

CROSS-REFERENCE TO RELATED APPLICATION

This application is a continuation application of PCT Application No. PCT/JP 2017/024345 filed on Jul. 3, 2017, which is hereby incorporated by reference in its entirety.

TECHNICAL FIELD

The disclosed technology relates to a treatment system having a medical device capable of grasping a treatment target between a pair of grasping jaws disposed at an end effector.

DESCRIPTION OF THE RELATED ART

US Patent Application 2015/0335347 A1 discloses a medical device that can grasp a body tissue such as a blood vessel between a pair of grasping jaws. With this medical device, the body tissue is grasped between the paired grasping jaws by an operation at a handle. With the treatment target grasped between the grasping jaws, electrical energy is supplied to the medial device by an operation at an operation button or the like, whereby treatment energy is applied to the treatment target grasped at an end effector.

With the medical device of US Patent Application 2015/0335347 A1, the appropriate magnitude of grasping force with which the treatment target is grasped differs depending on the kind of a body tissue as the treatment target, the size of the treatment target, the application conditions of treatment energy to be applied to the treatment target during the treatment, and so on. It is therefore required to adjust the grasping force to a magnitude suited for the treatment according to the heretofore-described conditions and the like.

BRIEF SUMMARY OF EMBODIMENTS

One aspect of the disclosed technology is directed to a medical device comprises a housing and an elongated sheath having opposed respective proximal and distal ends extending along a longitudinal axis and being attached from the proximal end to the housing. An end effector is configured to be attached to the distal end portion of the sheath. The end effector includes a pair of grasping jaws capable of be openable and closable with respect to one another. A movable shaft includes a distal end that being connected at to the end effector and configured to be movable with respect to the sheath along the longitudinal axis so as to cause the paired grasping jaws to be opened or closed with respect to one another. A movable handle is configured to pivot with respect to the housing via an axis of pivot and having an input position where an operation is inputted so as to cause the handle to pivot. The movable shaft and the movable handle are configured such that at least one of a first length from the axis of pivot to the input position and a second length from the axis of pivot to an acting position where a driving force acts to move the movable shaft is changeable in an initial state before the operation is inputted at the input position.

Another aspect of the disclosed technology is directed to a treatment system comprises a housing and an elongated sheath having opposed respective proximal and distal ends extending along a longitudinal axis and being attached from the proximal end to the housing. An end effector is configured to be attached to the distal end portion of the sheath. The end effector includes a pair of grasping jaws capable of be openable and closable with respect to one another. A movable shaft includes a distal end that being connected at to the end effector and configured to be movable with respect to the sheath along the longitudinal axis so as to cause the paired grasping jaws to be opened or closed with respect to one another. A movable handle is configured to pivot with respect to the housing via an axis of pivot, and having an input position where an operation is inputted so as to cause the handle to pivot. A first operation member is configured to input an operation to supply electrical energy to the medical device in a first supply mode. A second operation member is configured to supply electrical energy to the medical device in a second supply mode that is different from the first supply mode. An actuator is configured to move the moving member relative to the movable handle. A processor is configured to control operation of the actuator such that the moving member is controlled in driven state so as to adjust the second length. The movable shaft and the movable handle are configured such that at least one of a first length from the axis of pivot to the input position and a second length from the axis of pivot to an acting position where a driving force acts to move the movable shaft is changeable in an initial state before the operation is inputted at the input position. The movable shaft and the movable handle are configured such that the second length has a first value based on an input of the operation at the first operation member or the second length has a second value, which is different from the first value, based on an input of the operation at the second operation member.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

The disclosed technology has as an object thereof the provision of a treatment instrument that can adjust a grasping force for a treatment target, which is grasped between a pair of grasping jaws, to an appropriate magnitude. The disclosed technology also has as another object thereof the provision of a treatment system including the treatment instrument.

First Embodiment

Figure 1:
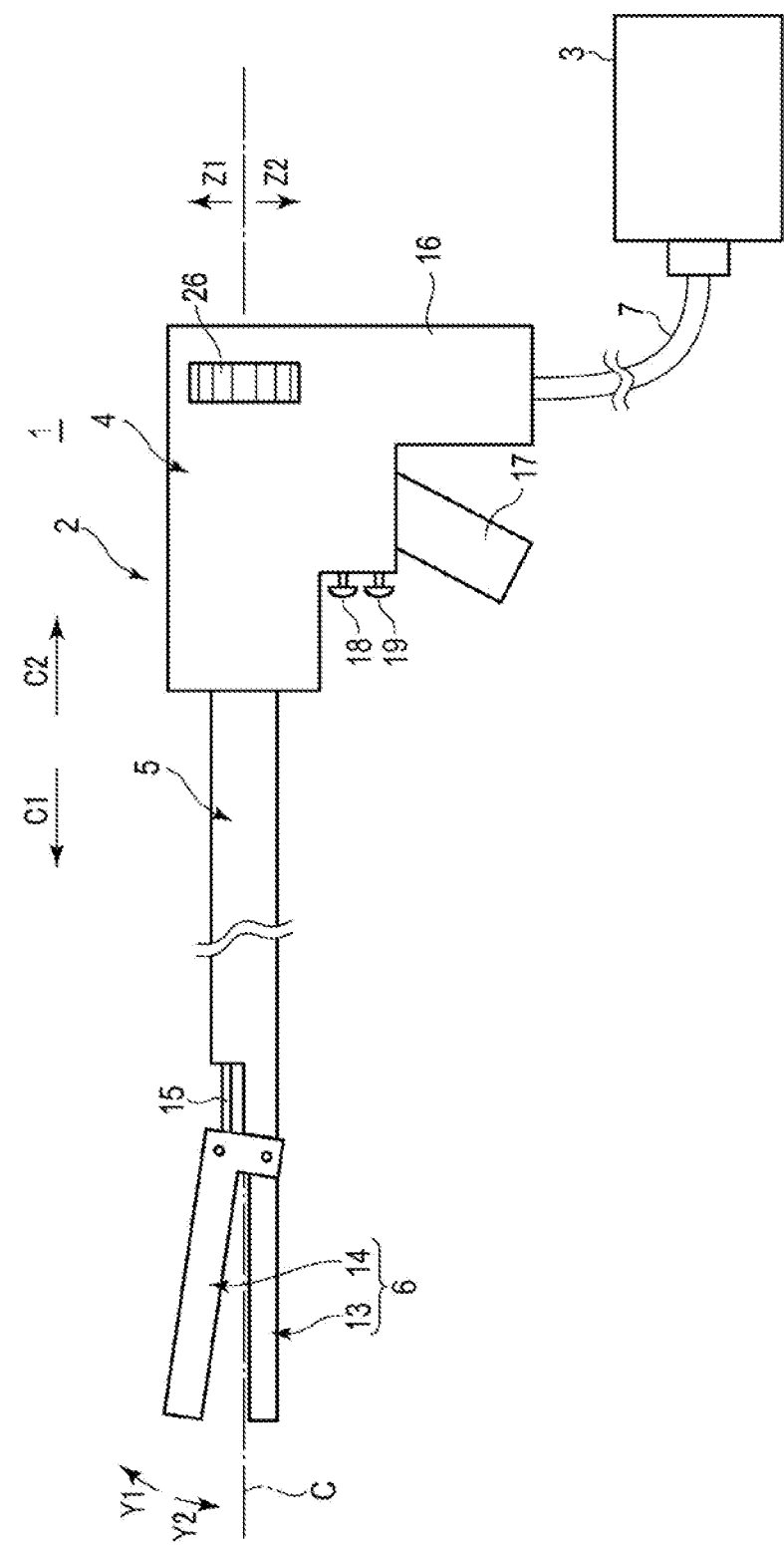
FIG. 1 is a view schematically illustrating a medical device according to a first embodiment.

With reference to FIGS. 1 to 4, a description will be made about the first embodiment of the disclosed technology. FIG. 1 is a view illustrating a treatment system 1 in which a treatment instrument 2 as a medical device of this embodiment is used. As illustrated in FIG. 1, the treatment system 1 includes the treatment instrument 2 and a power source device 3. The treatment instrument 2 includes a housing 4, a shaft 5, i.e., sheath, connected to a distal end side of the housing 4, and an end effector 6 disposed on a distal end portion of the shaft 5. A cable 7 is connected at an end thereof to the housing 4. The cable 7 is detachably connected at an opposite end thereof to the power source device 3. The shaft 5 is disposed extending with a longitudinal axis C as a central axis. Here, a direction along the longitudinal axis C is assumed to be a longitudinal direction. Further, a side in the longitudinal direction is assumed to be a distal end side (a side indicated by arrow C1) while an opposite side is assumed to be a proximal end side (a side indicated by arrow C2).

A grip 16, i.e., fixed handle, is disposed on the housing 4, and a handle 17, i.e., movable handle, is pivotally, i.e., turnably, attached to the housing 4. The grip 16 is disposed extending in a direction that the grip 16 intersects, i.e., is substantially perpendicular to, the longitudinal axis C, and the direction in which the grip 16 is disposed extending (a direction toward a side indicated by arrow Z1 and a side indicated by arrow Z2) intersects, i.e., is substantially perpendicular to, the longitudinal axis C. The handle 17, i.e., first handle, is pivotally connected to the housing 4. The handle 17 pivots relative to the housing 4, whereby the handle 17 opens or closes relative to the grip 16. Now, a direction which intersects, i.e., is substantially perpendicular to, the longitudinal axis C and also intersects, i.e., is substantially perpendicular to, the direction in which the grip 16 is disposed extending is assumed to be a width direction of the housing 4.

The end effector 6 includes a pair of grasping jaws 13 and 14, i.e., clamping members. The first grasping jaw 13 and the second grasping jaw 14 are openable and closable relative to each other. In this embodiment, the first grasping jaw 13 is attached to the shaft 5, and the second grasping jaw 14 is pivotally attached to the distal end portion of the shaft 5. In another example, the first grasping jaw 13 and the second grasping jaw 14 are both pivotally attached to the shaft 5.

The handle 17 and the second grasping jaw 14 are connected together via a movable shaft 15 disposed extending in the longitudinal direction inside the shaft 5. The handle 17 opens or closes relative to the grip 16, whereby the movable shaft 15 moves relative to the shaft 5 and the housing 4 in the longitudinal direction to open or close between the paired grasping jaws 13 and 14. The handle 17 and the movable shaft 15 transmit a driving force to the end effector 6 such that the grasping jaws 13 and 14 are opened or closed relative to each other.

The opening and closing direction of the end effector 6 intersects, i.e., is substantially perpendicular to, the longitudinal axis C. In the opening and closing direction of the end effector 6, a side toward which the second grasping jaw 14 opens relative to the first grasping jaw 13 will be called "an opening direction of the second grasping jaw 14 (a direction indicated by arrow Y1)," and a side toward which the second grasping jaw 14 closes relative to the first grasping jaw 13 will be called "a closing direction of the second grasping jaw 14 (a direction indicated by arrow Y2)."

To the housing 4, operation buttons 18 and 19 are attached as operation members. The operation buttons 18 and 19 are each an operation input portion where an operation is inputted to supply electrical energy from the power source device 3 to the treatment instrument 2. An operation is inputted to the operation button 18 or 19 with a treatment target grasped between the grasping jaws 13 and 14, whereby electrical energy is supplied to the treatment instrument 2 from the power source device 3 to apply treatment energy to the treatment target grasped between the grasping jaws 13 and 14. In an example, a footswitch or the like which is discrete from the treatment instrument 2 is disposed, instead of the operation buttons 18 and 19 or in addition to the operation buttons 18 and 19, as an operation member where an operation is inputted to supply electrical energy from the power source device 3 to the treatment instrument 2.

Figure 2A:
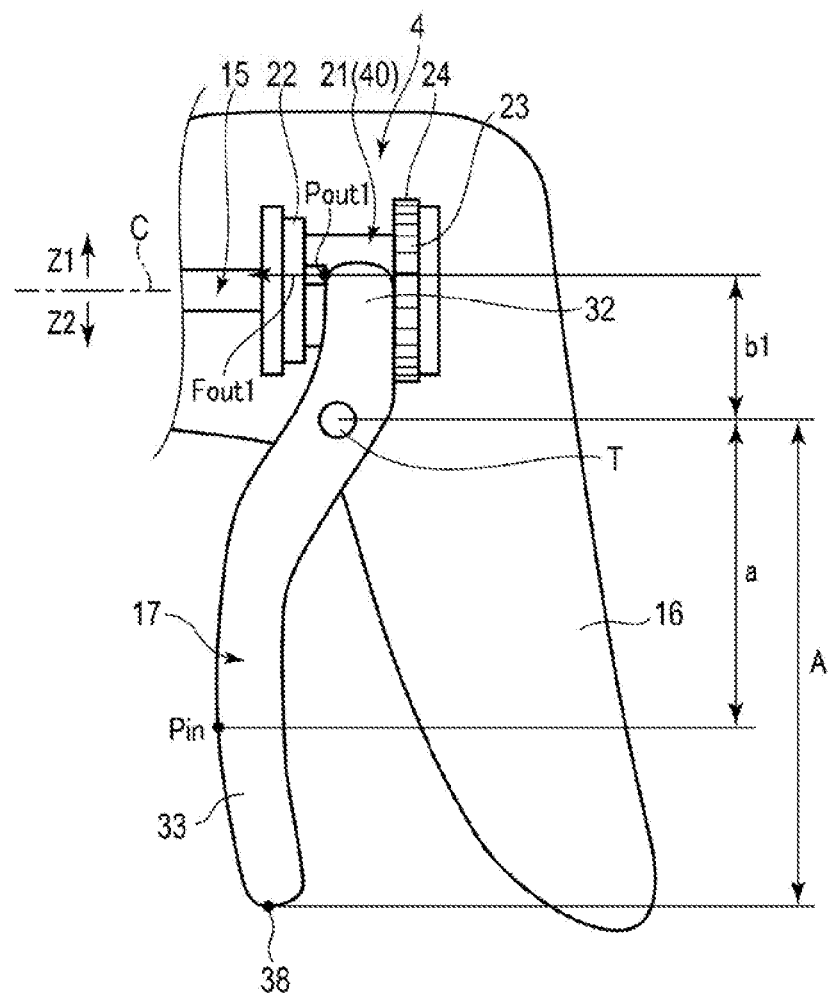
FIG. 2A is a view schematically illustrating a state in which a protrusion of a rotor in the first embodiment is located at a first position.
Figure 2B:
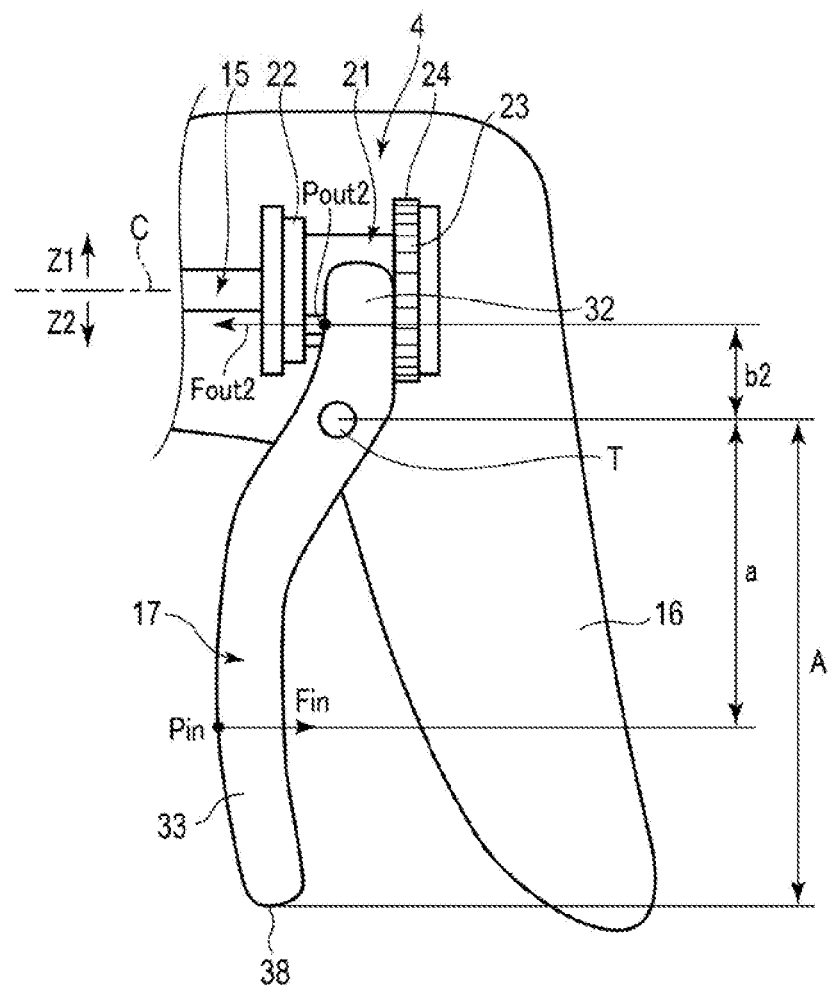
FIG. 2B is a view schematically illustrating a state in which the protrusion of the rotor in the first embodiment is located at a second position.

As illustrated in FIGS. 2A and 2B, the handle 17 includes an engagement portion 32 connected to the movable shaft 15 at a position inside the housing 4, an extending portion 33 extending from the housing 4 to an outside thereof, and a fulcrum position T to be used as a turning axis, i.e., pivot, relative to the housing 4. The extending portion 33 is disposed on the proximal end side relative to the grip 16. The fulcrum position T is located between the engagement portion 32 and the extending portion 33. When the handle 17 pivots relative to the housing 4 about the fulcrum position T, the engagement portion 32 and the extending portion 33 therefore move to opposite sides, respectively, relative to the housing 4 in the longitudinal direction.

The extending portion 33 is moved relative to the housing 4 toward the proximal end side, in other words, toward the grip 16 by an operation at the handle 17, whereby the handle 17 pivots relative to the housing 4 about the fulcrum position T, so that the engagement portion 32 of the handle 17 and the movable shaft 15 move together relative to the housing 4 and the shaft 5 toward the distal end side. As a consequence, the grasping jaws 13 and 14 close together at the end effector 6 connected to a distal end portion of the movable shaft 15.

The extending portion 33 has an input position Pin where an operation is inputted to close the handle 17 relative to the grip 16. The input position Pin is located on the handle 17 between the fulcrum position T and an extension end 38 of the extending portion 33 of the handle 17, the extending portion 33 extending from the housing 4. Depending on the size or the like of a surgeon's hand, the input position Pin can move within the extending portion 33. During the same treatment by the same surgeon, however, the input position Pin remains at substantially the same location. At the input position Pin, an operating force Fin is inputted when the surgeon presses the handle 17 toward the grip 16. In other words, the input position Pin is used as a point of effort, where the operating force Fin inputted to the handle 17 is inputted upon transmission of the operating force Fin to the movable shaft 15. Now, the length between the fulcrum position T and the extension end 38 is assumed to be a distance A, i.e., first length. The distance between the fulcrum position T and the input position Pin is assumed to be a distance a.

The treatment instrument 2 includes a moving member 40, i.e., leverage adjustment mechanism. In this embodiment, a rotating body 21, i.e., rotor, is mounted as the moving member 40 on the movable shaft 15.

The rotating body 21 is substantially cylindrical and is disposed along the longitudinal axis C. The rotating body 21 has a central axis which is substantially coincident with the longitudinal axis C. The rotating body 21 moves together with the movable shaft 15 relative to the housing 4 in the longitudinal direction. Further, the rotating body 21 is disposed inside the housing 4 in a state that the rotating body 21 is rotatable about the longitudinal axis C.

The rotating body 21 includes, on a distal end portion thereof, a flange portion 22 extending from an outer circumferential surface toward an outer circumferential side of the rotating body 21. The rotating body 21 also includes, on a proximal end portion thereof, a flange portion 23 extending from the outer circumferential surface toward the outer circumferential side of the rotating body 21. The flange portion 23 includes an engagement portion 24, i.e., gear, on an outer circumference thereof.

The housing 4 includes an operation knob 26, i.e., operation dial. At the operation knob 26, an operation is inputted to cause rotation of the rotating body 21 about the longitudinal axis C. The operation knob 26 has an axis of rotation which is substantially parallel to the longitudinal axis C. In this embodiment, the axis of rotation of the operation knob 26 substantially coincides with the longitudinal axis C. Therefore, the operation knob 26 is rotatable relative to the housing 4 about the longitudinal axis C.

Figure 3:
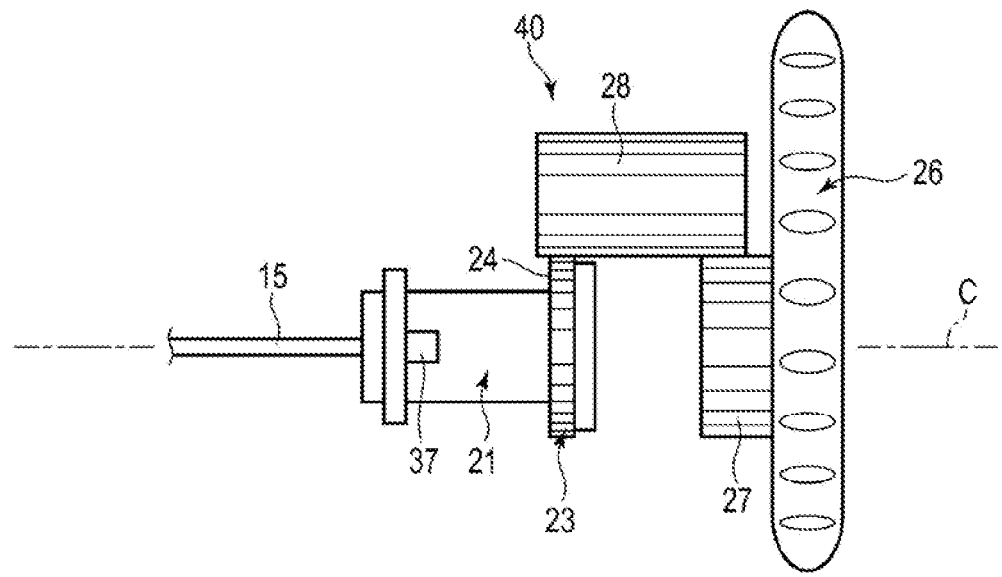
FIG. 3 is a view schematically illustrating a connection structure between an operation knob and the rotor in the first embodiment.

As illustrated in FIG. 3, the operation knob 26 and the rotating body 21 are connected to each other by an engaging member 27, i.e., gear, and an engaging member 28. The engaging member 27, i.e., gear, is attached to the operation knob 26, while the engaging member 28 is in engagement with both the rotating body 21 and the engaging member 27. The rotating body 21 and the engaging member 28 are connected together through engagement, i.e., meshing, of the engagement portion 24 of the flange portion 23 and the engaging member 28. Further, the engagement portion 24 is movable relative to the engaging member 28 in the longitudinal direction while maintaining the engagement with the engaging member 28. Accordingly, the rotating body 21 is movable together with the movable shaft 15 relative to the housing 4 in the longitudinal direction while being maintained in engagement with the engaging member 28.

When an operation is inputted at the operation knob 26, the operation knob 26 rotates relative to the housing 4 about the longitudinal axis C. The resulting rotational driving force of the operation knob 26 is transmitted to the rotating body 21 via the engaging member 27, the engaging member 28, and the engagement portion 24, whereby the rotating body 21 rotates relative to the housing 4 about the longitudinal axis C.

Figure 4:
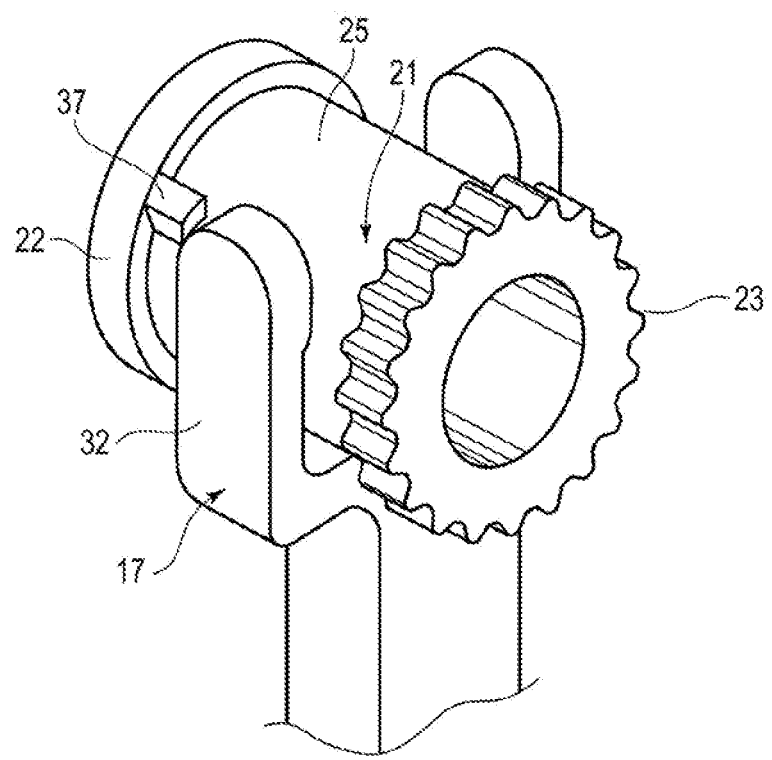
FIG. 4 is a perspective view schematically illustrating the rotor in the first embodiment.

As illustrated in FIG. 4, a groove portion 25 is formed between the flange portions 22 and 23. The groove portion 25 is recessed toward the longitudinal axis C. The groove portion 25 is disposed extending in the longitudinal direction and is formed over the entire circumference thereof about the longitudinal axis C. The engagement portion 32 of the handle 17 is in engagement with the groove portion 25. The handle 17 is attached to the rotating body 21 and the movable shaft 15 by engagement of the engagement portion 32 with the groove portion 25.

On the groove portion 25 of the rotating body 21, a protrusion 37, i.e., engagement portion, is disposed protruding toward an outer side of the rotating body 21. The protrusion 37 is disposed on the groove portion 25 at a location near the flange portion 22. The protrusion 37 is also disposed between the engagement portion 32 of the handle 17 and the flange portion 22 as viewed in the longitudinal direction. The rotating body 21 rotates relative to the movable shaft 15 and the handle 17 about the longitudinal axis C, whereby the position, i.e., angular position, of the protrusion 37 changes relative to the movable shaft 15 and the handle 17 about the longitudinal axis C. By the rotation of the rotating body 21 relative to the movable shaft 15 and the handle 17 about the longitudinal axis C, the position of the protrusion 37 also changes relative to the handle 17 in an extending direction of the grip 16.

When the extending portion 33 of the handle 17 is pressed toward the grip 16 by an operation at the handle 17, the engagement portion 32 of the handle 17 comes into contact with the protrusion 37 from the proximal end side at the groove portion 25. The engagement portion 32 of the handle 17 then presses the protrusion 37 toward the distal end side. A driving force Fout acts from the handle 17 to the rotating body 21 via the protrusion 37. The driving force Fout outputted from the handle 17 is then transmitted to the movable shaft 15 via the rotating body 21. At the contact position between the engagement portion 32 of the handle 17 and the protrusion 37, the driving force Fout is hence outputted from the handle 17 to the rotating body 21. Accordingly, the contact position between the engagement portion 32 and the protrusion 37 is a point of action, where the driving force Fout is outputted from the handle 17 to the rotating body 21 when the operating force Fin inputted to the handle 17 is transmitted to the rotating body 21, and is also an acting position Pout, where the driving force Fout that is to drive the movable shaft 15 is caused to act from the handle 17 to the movable shaft 15. The protrusion 37 can come into contact with the handle 17, and forms the acting position Pout of the driving force Fout from the handle 17 to the movable shaft 15. Now, the length between the fulcrum position T and the acting position Pout is assumed to be a distance b, i.e., second length.

By the principle of lever as applied to the fulcrum position T as a fulcrum, a relation of a·Fin=b·Fout, that is, Fout=Fin·(a/b) is established between the operation force Fin inputted at the input position Pin and the driving force Fout outputted from the handle 17 to the rotating body 21 at the acting position Pout. Therefore, the magnitude of the driving force Fout to be outputted to the rotating body 21 upon input of the operating force Fin at the handle 17 is determined by a transmission ratio H (=a/b) that is a ratio of the distance a to the distance b. The ratio of the distance A to the distance b will be called "leverage K" (=A/b).

For example, the greater the distance b, the smaller the transmission ratio H and the leverage K, and so the driving force Fout. On the other hand, the smaller the distance b, the greater the transmission ratio H and the leverage K, and so the driving force Fout.

The driving force Fout acted to the rotating body 21 is transmitted from the rotating body 21 to the movable shaft 15. Therefore, the rotating body 21 can transmit the driving force Fout, which has been outputted from the handle 17, to the movable shaft 15. Then, the driving force Fout transmitted to the movable shaft 15 is transmitted to the end effector 6 to which the movable shaft 15 is connected at the distal end portion thereof, and affects the grasping force to be applied to the treatment target grasped between the grasping jaws 13 and 14. The driving force Fout transmitted to the rotating body 21 and the movable shaft 15 hence affects the grasping force to the treatment target grasped between the grasping jaws 13 and 14. For example, the greater the driving force Fout transmitted to the rotating body 21 and the movable shaft 15, the greater the grasping force between the grasping jaws 13 and 14.

A description will next be made about the operation and advantageous effects of the treatment instrument 2 of this embodiment. Upon conducting treatment with the treatment instrument 2, the surgeon performs an operation input at the operation knob 26 according to conditions such as the kind of a body tissue to be treated, e.g., a blood vessel, a lymph vessel or the like, the size of a blood vessel or the like, and the kind of the blood vessel. The surgeon then inserts the end effector 6 into a body cavity such as the abdominal cavity, and with a treatment target such as a blood vessel disposed between the grasping jaws 13 and 14, an operation is inputted at the handle 17 to close the end effector 6. As a consequence, the treatment target is grasped between the grasping jaws 13 and 14, and a grasping force is applied to the treatment target grasped between the grasping jaws 13 and 14. An operation input is then performed at one of the operation buttons 18 and 19 with the treatment target grasped between the grasping jaws 13 and 14, whereby electrical energy is outputted from the power source device 3 to the treatment instrument 2 to apply treatment energy to the treatment target.

When the operation knob 26 is rotated about an axis of rotation thereof, i.e., the longitudinal axis C, by an operation input at the operation knob 26, the resulting rotational driving force of the operation knob 26 is transmitted to the rotating body 21, so that the rotating body 21 rotates relative to the housing 4 about the longitudinal axis C. By the rotation of the rotating body 21 about the longitudinal axis C, the position, i.e., angular position, of the protrusion 37 changes about the longitudinal axis C. By the change of the position of the protrusion 37 about the longitudinal axis C, the position of the protrusion 37 also changes relative to the handle 17 in the extending direction of the grip 16.

As illustrated in FIG. 2A, for example, the handle 17 and the protrusion 37 are in contact with each other at a first acting position Pout1, i.e., first contact position, when the protrusion 37 is located at a first position, i.e., first angular position, about the longitudinal axis C. At this time, the first acting position Pout1 is located apart by a first value b1 from the fulcrum position T. Further, the transmission ratio H has a first value H1 (=a/b1), and the leverage K has a first value K1 (=A/b1). When the operating force Fin is inputted at the handle 17 at the input position Pin, a first driving force Fout1 (=Fin·H1) therefore acts toward the distal end side on the movable shaft 15 at the first acting position Pout1 via the protrusion 37 of the rotating body 21.

As illustrated in FIG. 2B, on the other hand, the handle 17 and the protrusion 37 are in contact with each other at a second acting position Pout2, i.e., second contact position, different from the first acting position Pout1 when the protrusion 37 is located at a second position, i.e., second angular position, different from the first position, i.e., first angular position, about the longitudinal axis C. At this time, the second acting position Pout2 is located apart by a second value b2 smaller than the first value b1 from the fulcrum position T. Further, the transmission ratio H has a second value H2 (=a/b2) greater than the first value H1, and the leverage K has a second value K2 (=A/b2) greater than the first value K1. When the operating force Fin is inputted to the handle 17 at the input position Pin, a second driving force Fout2 greater than the first driving force Fout1 therefore acts toward the distal end side on the movable shaft 15 at the second acting position Pout2 via the protrusion 37 of the rotating body 21.

As described hereinbefore, the contact position Pout, i.e., acting position, between the rotating body 21 as the moving member 40 and the handle 17 changes in this embodiment when the rotating body 21 is driven. As a consequence, the distance b, i.e., second length, from the fulcrum position T to the acting position Pout changes, and the transmission ratio H and the leverage K change. By the changes in the transmission ratio H and the leverage K, the magnitude of the driving force Fout to be transmitted from the handle 17 to the rotating body 21 and the movable shaft 15 changes upon input of the operating force Fin at the handle 17. By the change in the driving force Fout to be transmitted to the movable shaft 15, the magnitude of a driving force to be transmitted to the end effector 6 changes, leading to a change in the magnitude of a grasping force, i.e., the amount of a grasping force, to be applied to the treatment target grasped between the grasping jaws 13 and 14.

Therefore, the surgeon can switch the grasping force to the treatment target, which is grasped between the grasping jaws 13 and 14, by switching the state of driving of the moving member 40 according to the kind, size and the like of the grasped treatment target.

First Modification of First Embodiment

Figure 5:
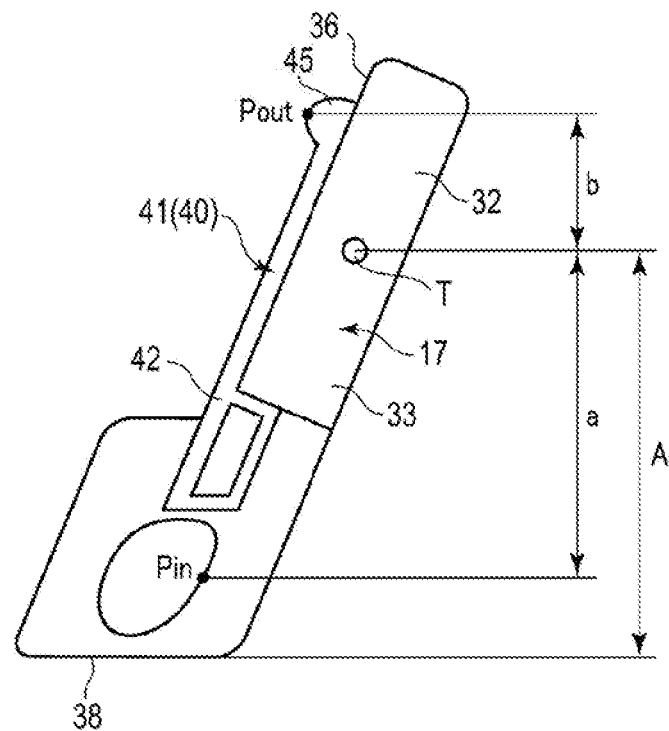
FIG. 5 is a view schematically illustrating a handle in a first modification of the first embodiment.

FIG. 5 is a view illustrating a first modification of this embodiment.

In this modification, a movable bar 41, i.e., bar member, is disposed as the moving member 40. In this modification, the heretofore-described rotating body 21 is not disposed, and the handle 17 is directly attached to the movable shaft 15. Further, similar flange portions 22 and 23 and groove portion 25 as in the first embodiment are arranged on the movable shaft 15.

The movable bar 41 is attached to a distal end face 36 of the handle 17 from the distal end side. The movable bar 41 is movable relative to the handle 17 along the distal end face 36 of the handle 17. Further, the movable bar 41 includes an operating portion 42. At the operating portion 42, an operation is inputted to move the movable bar 41 relative to the handle 17. The operating portion 42 is disposed near the extending portion 33 of the handle 17 outside the housing 4.

The movable bar 41 includes a protrusion 45 that protrudes toward the distal end side. The protrusion 45 is disposed on the engagement portion 32. By performing an operation at the operating portion 42, the protrusion 45 is moved relative to the handle 17 in the extending direction of the grip 16.

In this modification, the protrusion 45 disposed on the engagement portion 32 of the handle 17 comes into contact with the flange portion 22 of the movable shaft 15 from the proximal end side when the extending portion 33 of the handle 17 is pressed toward the grip 16 by an operation at the handle 17. The protrusion 45 then presses the flange portion 22 toward the distal end side. To the movable shaft 15, a driving force Fout is transmitted from the handle 17 via the protrusion 45. The driving force Fout outputted from the handle 17 is then transmitted to the movable shaft 15 via the movable bar 41. At the contact position between the protrusion 45 and the flange 22, the driving force Fout is therefore outputted from the handle 17 to the movable shaft 15 via the protrusion 45. Accordingly, the contact position between the protrusion 45 and the flange portion 22 is used as an acting position Pout where the driving force Fout, which is to drive the movable shaft 15, is caused to act from the handle 17 to the movable shaft 15. Therefore, the protrusion 45 of the movable bar 41 forms the acting position Pout.

In this modification, the movable bar 41 as the moving member 40 is moved relative to the handle 17 by an operation input at the operating portion 42, whereby the protrusion 45 moves relative to the handle 17 in the extending direction of the grip 16. As a consequence, the position of the protrusion 45 changes relative to the handle 17 in the extending direction of the grip 16, leading to a change in the acting position Pout of the driving force Fout from the handle 17 to the movable shaft 15. As a consequence, as in the first embodiment, the distance b between the fulcrum position T and the acting position Pout, the transmission ratio H, and the leverage K change, so that the magnitude of the driving force to be transmitted from the handle 17 to the end effector 6 via the movable bar 41 and the movable shaft 15 changes. As a consequence, the magnitude of a grasping force to be applied to a treatment target grasped between the grasping jaws 13 and 14 also changes.

Second Modification of First Embodiment

Figure 6:
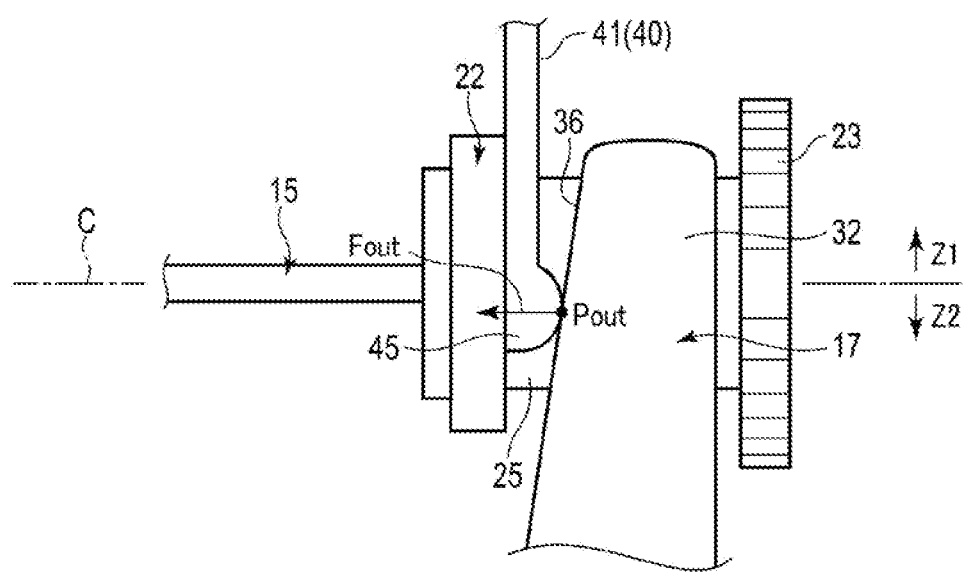
FIG. 6 is a view schematically illustrating a state in which a handle in a second modification of the first embodiment is pressing a moving member.

As illustrated as a second modification of this embodiment in FIG. 6, a movable bar 41 may be attached to the housing 4 instead of the handle 17. In this case, an operating portion 42 of the movable bar 41 is exposed to the outside from the housing 4, and enables to input an operation to move the movable bar 41 relative to the housing 4 and the handle 17. Further, the movable bar 41 is disposed along a proximal end face of the flange portion 22 of the movable shaft 15. By an operation input at the operating portion 42, the movable bar 41 is moved along the proximal end face of the flange portion 22 in the extending direction of the grip 16. In addition, a protrusion 45 protrudes toward the proximal end side and is disposed between the flange portion 22 and the handle 17. The engagement portion 32 of the handle 17 comes into contact with the protrusion 45 from the proximal end side, whereby a driving force Fout acts toward the distal end side to the protrusion 45 from the handle 17 and the driving force is transmitted to the movable shaft 15 via the movable bar 41. At the contact position between the engagement portion 32 of the handle 17 and the protrusion 45, a driving force Fout is hence outputted from the handle 17 to the movable shaft 15 via the protrusion 45. Accordingly, the contact position between the protrusion 45 and the engagement portion 32 is used as an acting position Pout where the driving force Fout, which is to drive the movable shaft 15, is caused to act from the handle 17 to the movable shaft 15. Therefore, the protrusion 45 of the movable bar 41 forms the acting position Pout.

In this modification, the movable bar 41 as the moving member 40 is driven by an operation input at the operating portion 42, whereby the protrusion 45 moves relative to the handle 17 in the extending direction of the grip 16, and the contact position, i.e., acting position Pout, between the handle 17 and the movable bar 41 changes. As a consequence, as in the first embodiment, the distance b between the fulcrum position T and the acting position Pout, the transmission ratio H, and the leverage K change, so that the magnitude of the driving force to be transmitted from the handle 17 to the end effector 6 via the movable bar 41 and the movable shaft 15 changes. As a consequence, the magnitude of a grasping force to be applied to a treatment target grasped between the grasping jaws 13 and 14 also changes.

Third Modification of First Embodiment

Figure 7:
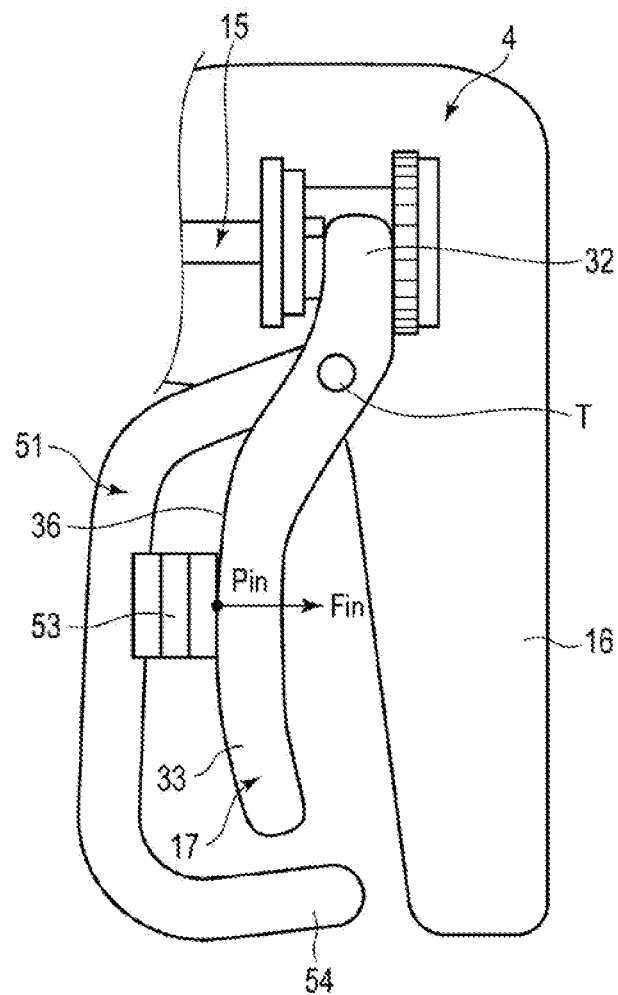
FIG. 7 is a view schematically illustrating a handle in a third modification of the first embodiment.

FIG. 7 is a view illustrating a third modification of this embodiment.

In this modification, a second handle 51, i.e., auxiliary handle, is attached to the handle 17. The second handle 51 is pivotally attached at an end thereof to the handle 17. In this modification, the second handle 51 has a pivot which is substantially coincident with the pivot T of the handle 17 relative to the housing 4. On the distal end side relative to the handle 17, the second handle 51 is disposed facing the distal end face 36 of the handle 17.

Between the second handle 51 and the handle 17, a spring 53 is disposed as an elastic member. The spring 53 is connected at an end thereof to or is in contact at the end thereof from the distal end side with the distal end face 36 of the handle 17. The spring 53 is connected at an opposite end thereof to or is in contact at the opposite end thereof from the proximal end side with the second handle 51. In a natural state, i.e., with a natural length, or in a state of being compressed to a certain extent from the natural state, i.e., a normal state, the spring 53 is disposed between the handle 17 and the second handle 51. The handle 17 and the second handle 51 are spaced from each other owing to the disposition of the spring 53.

The second handle 51 includes an extending portion 54 that extends toward a side on which the handle 17 is disposed. The extending portion 54 extends beyond the handle 17 to a position on the proximal end side.

Upon inputting an operation to close the grasping jaws 13 and 14 together, the surgeon presses the second handle 51 toward the proximal end side, that is, toward the grip 16. When the second handle 51 is pressed toward the proximal end side, a driving force is transmitted from the second handle 51 to the extending portion 33 of the handle 17 via the spring 53, so that the handle 17 pivots relative to the housing 4. At this time, the second handle 51 moves together with the extending portion 33 of the handle 17 toward the proximal end side, that is, toward the grip 16. By the pivotal movement of the handle 17 relative to the housing 4, the engagement portion 32 of the handle 17 and the movable shaft 15 move together toward the distal end side relative to the housing 4 and the shaft 5, and the end effector 6 closes, as in the first embodiment and the like. As is appreciated from the foregoing, the handle 17 is not directly pressed but is indirectly pressed via the second handle 51 by the surgeon in this modification.

When a treatment target is compressed to a certain extent between the grasping jaws 13 and 14, the closing operation of the end effector 6 stops, and at the same time, the movement of the movable shaft 15 relative to the housing 4 and the shaft 5 toward the distal end side and the pivotal movement, i.e., turning, of the handle 17 relative to the housing 4 also stop.

When the surgeon further presses the second handle 51 toward the grip 16 with the pivotal movement of the handle 17 relative to the housing 4 being stopped, the second handle 51 pivots relative to the handle 17. As a consequence, the second handle 51 moves toward the handle 17. The extending portion 54 of the second handle 51 then comes into contact with a contact member (not illustrated) arranged on the grip 16 or the like, whereby the second handle 51 and the grip 16 close together to stop the movement of the second handle 51 toward the handle 17. By the movement of the second handle 51 toward the handle 17, the spring 53 is further compressed from the natural state or the normal state at this time.

Now, representing an amount of displacement, i.e., an amount of compression, of the spring 53 from the natural state by x and a spring constant of the spring 53 by k, the handle 17 is pressed toward the proximal end side under an elastic force E ($=k \cdot x$) of the spring 53. Therefore, the elastic force E of the spring 53 is inputted as an operating force Fin to the handle 17 at the contact position with the spring 53. In this modification, the position on the handle 17, where the spring 53 is attached to the handle 17 or the handle 17 is in contact with the spring 53, is hence used as an input position Pin where the operating force Fin is inputted. In this modification, the distance a between the input position Pin and the fulcrum position T therefore remains substantially constant irrespective of the size of the surgeon's hand or the like.

In this modification, the operating force Fin ($=k \cdot x$) to be inputted to the handle 17 is determined by the spring constant k of the spring 53 and the amount of displacement x, i.e., the amount of compression, of the spring 53 in a state that the second handle 51 has been closed toward the grip 16. The operating force Fin to be inputted to the handle 17 thus remains substantially constant irrespective of the magnitude of a force applied to the second handle 51 by the surgeon if the spring constant k and the amount of displacement x are constant. In other words, this modification enables to maintain the operating force Fin, which is to be inputted to the handle 17, at a substantially constant magnitude owing to the disposition of the second handle 51 and the spring 53 on the handle 17. It is hence possible to more accurately adjust the magnitude of a grasping force, which is to be applied to the treatment target, upon adjustment of the grasping force by using the heretofore-described moving member 40.

If the extending portion 33 of the handle 17 is disposed on the proximal end side relative to the grip 16 and an operation to close the end effector 6 is performed by pressing the extending portion 33 toward the distal end side, that is, toward the grip 16, the second handle 51 and the spring 53 are attached to the extending portion 33 of the handle 17 on the proximal end side of the handle 17. In other words, the second handle 51 and the spring 53 are disposed on a side opposite to the side, on which the grip 16 is located, with respect to the handle 17.

Fourth Modification of First Embodiment

Figure 8:
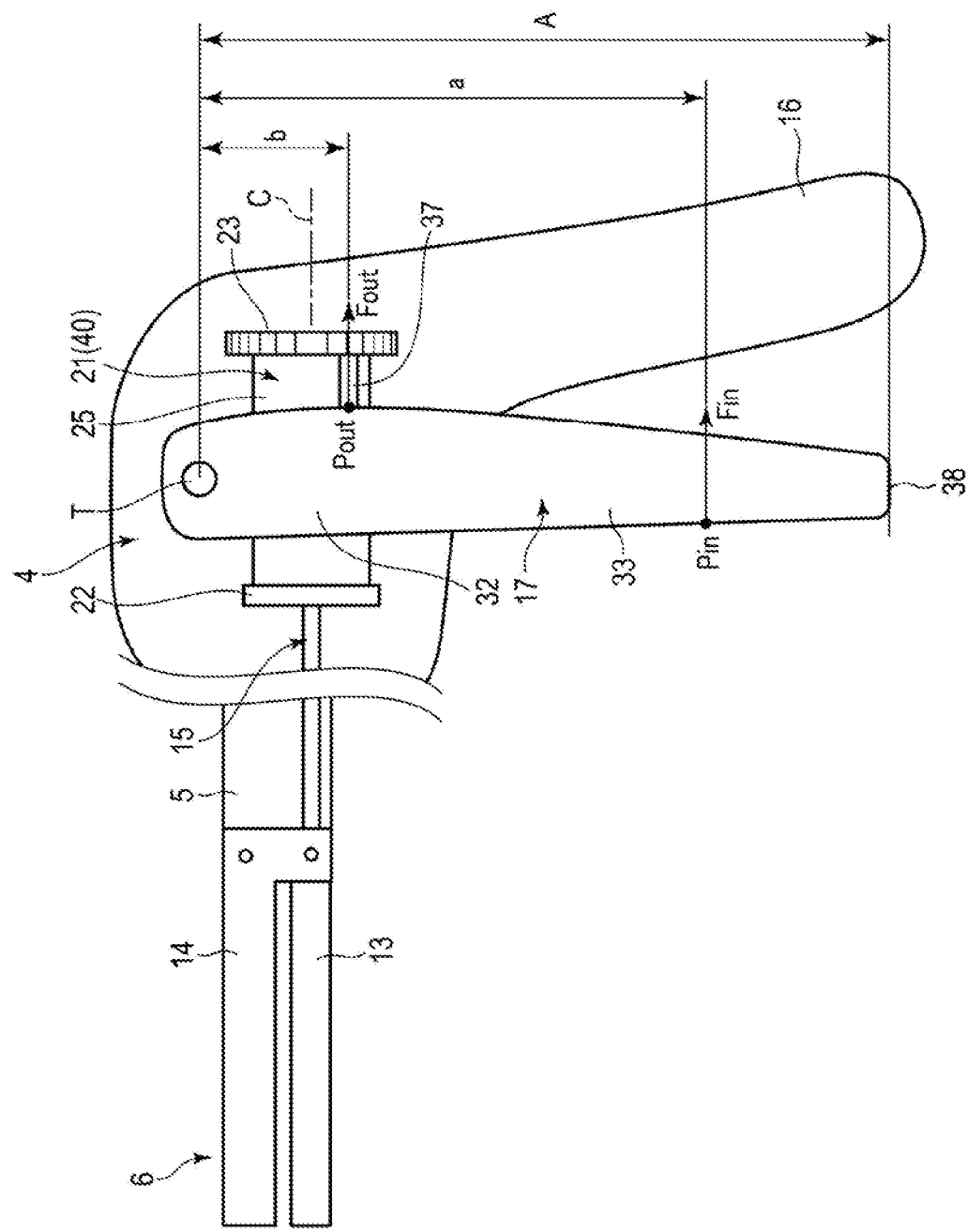
FIG. 8 is a view schematically illustrating an inside of a housing in a fourth modification of the first embodiment.

FIG. 8 is a view illustrating a fourth modification of this embodiment.

In a treatment instrument 2 of this modification, the grasping jaws 13 and 14 are closed together by a movement of the movable shaft 15 toward the proximal end side relative to the housing 4 and the shaft 5. As illustrated in FIG. 8, the handle 17 has a fulcrum position T located on a side opposite to the extending portion 33, which extends to the outside of the housing 4, with respect to the engagement portion 32 that is brought into engagement with the movable shaft 15. Therefore, the engagement portion 32 is located between the extending portion 33 and the fulcrum position T. In this modification, when the handle 17 pivots relative to the housing 4 about the fulcrum position T, the engagement portion 32 and the extending portion 33 move relative to the housing 4 in the longitudinal direction toward substantially the same side.

In this modification, a protrusion 37 is disposed on the groove portion 25 at a position near the flange portion 23, and is located between the flange portion 23 and the engagement portion 32 of the handle 17 as viewed in the longitudinal direction. When the extending portion 33 of the handle 17 is pressed toward the grip 16 by an operation at the handle 17, the engagement portion 32 of the handle 17 comes into contact with the protrusion 37 from the distal end side, and presses the protrusion 37 toward the proximal end side. A driving force Fout acts toward the proximal end side from the handle 17 to the rotating body 21 via the protrusion 37. The driving force Fout outputted from the handle 17 is then transmitted to the movable shaft 15 via the rotating body 21. At the contact position between the engagement portion 32 of the handle 17 and the protrusion 37, the driving force Fout is hence outputted from the handle 17 to the movable shaft 15 via the protrusion 37. The contact position between the protrusion 37 and the engagement portion 32 is therefore used as an acting position Pout where the driving force Fout, which is to drive the movable shaft 15, is caused to act from the handle 17 to the movable shaft 15. Therefore, the protrusion 37 of the rotating body 21 forms the acting position Pout.

Also, in this modification, the rotating body 21 as the moving member 40 is driven, whereby the rotating body 21 rotates about the longitudinal axis C and the position, i.e., angular position, of the protrusion 37 changes about the longitudinal axis C. By the change of the position of the protrusion 37 about the longitudinal axis C, the position of the protrusion 37 then changes relative to the handle 17 in the extending direction of the grip 16, so that the contact position, i.e., the acting position Pout, between the rotating body 21 and the handle 17 changes. As a consequence, as in the first embodiment, the distance b between the fulcrum position T and the acting position Pout, the transmission ratio H, and the leverage K change, so that the magnitude of the driving force to be transmitted from the handle 17 to the end effector 6 via the rotating body 21 and the movable shaft 15 changes. As a consequence, the magnitude of a grasping force between the grasping jaws 13 and 14 changes.

Second Embodiment

Figure 9:
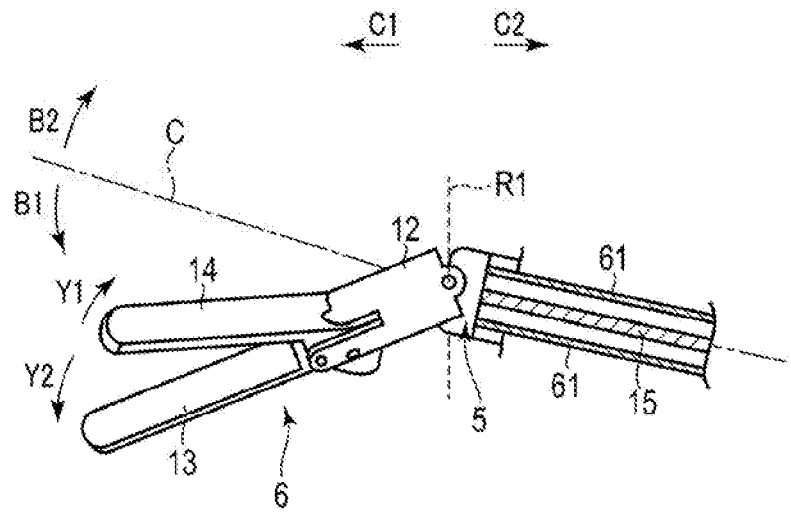
FIG. 9 is a view schematically illustrating an example of a configuration of a distal end portion of a shaft and an end effector in a second embodiment.

With reference to FIG. 9, a description will be made about a second embodiment of the disclosed technology. The second embodiment is similar in configuration to the first embodiment except for modifications to be described hereinafter. The same elements as in the first embodiment are identified by the same numeral references, and their description is omitted. A treatment instrument 2 of this embodiment has an end effector 6 that is bendable relative to the shaft 5.

As illustrated in FIG. 9, the end effector 6 includes an effector base 12 attached to the shaft 5, a first grasping jaw 13 fixed to the effector base 12, and a second grasping jaw 14 pivotally connected to the effector base 12. The effector base 12 is attached to the shaft 5 pivotally relative to the shaft 5 about a pivot R1, i.e., bending pivot. The pivot R1 intersects, i.e., is substantially perpendicular to, the longitudinal direction of the shaft 5 and is disposed extending in a parallel, i.e., substantially parallel, direction to the opening and closing direction of the grasping jaws 13 and 14. The end effector 6 with the effector base 12 included therein pivots relative to the shaft 5 about the pivot R1, whereby the end effector 6 is bent relative to the shaft 5 in a direction indicated by arrow B1 or arrow B2 in FIG. 9. In another example, a plurality of bending elements is disposed side by side in the longitudinal direction between the shaft 5 and the end effector 6, and the end effector 6 is formed to be bendable relative to the shaft 5.

In this embodiment, the operation knob 26 is arranged as a bending operation member through which an operation is inputted to bend the end effector 6 relative to the shaft 5. Further, a bending mechanism is arranged inside the treatment instrument 2. The operation knob 26 forms a part of the bending mechanism. A pair of wires 61, as elongated members, is connected at respective ends thereof to the bending mechanism. The wires 61 are disposed extending at opposite ends thereof through an inside of the shaft 5 toward the distal end side and are connected at the opposite ends thereof to the effector base 12 of the end effector 6. Through the bending mechanism, a rotary motion of the operation knob 26 is converted by a known mechanism to a linear motion in the longitudinal direction of the wires 61. By rotation of the operation knob 26 about the longitudinal axis C, the wires 61 are moved relative to the shaft 5 and the housing 4 in the longitudinal direction. At this time, the paired wires 61 move to opposite sides relative to each other in the longitudinal direction. As a consequence, the end effector 6 is bent relative to the shaft 5. The operation knob 26 and the wires 61 transmit a driving force to the end effector 6 such that the end effector 6 is bent relative to the shaft 5.

The grasping force between the grasping jaws 13 and 14 changes correspondingly to an axial force that acts from the movable shaft 15 to the end effector 6. The greater the driving force, i.e., axial force, transmitted from the movable shaft 15 to the end effector 6, the greater the grasping force. When the end effector 6 bends relative to the shaft 5, the movable shaft 15 bends at the distal end portion thereof. If the movable shaft 15 bends at the distal end portion thereof, the driving force to be transmitted through the movable shaft 15 is decomposed or is lost by friction or the like at the connected portion of the end effector 6 and the shaft 5. In a state that the end effector 6 is bent and the movable shaft 15 is bent at the distal end portion thereof, the driving force to be transmitted from the movable shaft 15 to the end effector 6 is reduced compared with that in a neutral state in which the movable shaft 15 is straight in its entirety. Further, the greater the bent angle, i.e., curved angle, of the end effector 6 to the shaft 5, the greater the reduction of the axial force by decomposition or the like of the force, and hence the smaller the driving force to be transmitted to the end effector 6. Accordingly, the greater the bent angle, i.e., curved angle, of the end effector 6 to the shaft 5, the smaller the grasping force between the grasping jaws 13 and 14.

When an operation is performed at the operation knob 26 to change the bent state of the end effector 6 relative to the shaft 5, the rotational driving force of the operation knob 26 is transmitted to the rotating body 21 via the engaging member 27 and the engaging member 28, so that the rotating body 21 rotates about the central axis, i.e., longitudinal axis C. At this time, the protrusion 37 disposed on the rotating body 21 also rotates together with the rotating body 21 about the longitudinal axis C. In this embodiment, the position, i.e., angular position, of the protrusion 37 about the longitudinal axis C and the position of the protrusion 37 relative to the handle 17 in the extending direction of the grip 16 hence change according to an operation input at the operation knob 26.

If the end effector 6 is not bent relative to the shaft 5, for example, in other words, if the end effector 6 and the shaft 5 extend straight as a whole, the end effector 6 is in a neutral state in which the bent angle of the end effector 6 to the shaft 5 is a first angle (=0°). At this time, the protrusion 37 (see FIG. 4) of the rotating body 21 is located at a first position, i.e., first angular position, about the longitudinal axis C as illustrated in FIG. 2A. At this time, a contact position, i.e., acting position Pout1, between the engagement portion 32 of the handle 17 and the protrusion 37 is located apart by the first value b1 from the fulcrum position T. At this time, the transmission ratio H has a first value H1 (=a/b1), and the leverage K has a first value K1 (=A/b1). To the rotating body 21 and the movable shaft 15, a first driving force Fout1 (=Fin·H1) is then transmitted from the handle 17.

If the end effector 6 is in a state of being bent relative to the shaft 5, on the other hand, the bent angle of the end effector 6 to the shaft 5 has a second angle greater than the first angle as illustrated in FIG. 9. At this time, the protrusion 37 of the rotating body 21 is located at a second position, i.e., angular position, which is different from the first position, i.e., the first angular position, about the longitudinal axis C as illustrated in FIG. 2B. At this time, the distance b between the acting position Pout and the fulcrum position T has a second value b2 smaller than the first value b1. At this time, the transmission ratio H has a second value H2 (=a/b2) greater than the first value H1 (=a/b1), and the leverage K has a second value K2 (=A/b2) greater than the first value K1 (=A/b1). To the rotating body 21 and the movable shaft 15, a second driving force Fout2 (=Fin·H2) greater than the first driving force Fout1 (=Fin·H1) is then transmitted from the handle 17.

If the end effector 6 is bent relative to the shaft 5, the driving force Fout to be transmitted to the rotating body 21 and the movable shaft 15 becomes greater than that if the end effector 6 is in the neutral state. In a state that the transmission efficiency of a driving force from the movable shaft 15 to the end effector 6 has decreased due to bending of the end effector 6, the driving force Fout to be transmitted to the movable shaft 15 increases accordingly. The effect of a decrease in the transmission efficiency of an axial force from the movable shaft 15 to the end effector 6 by bending of the end effector 6 is hence canceled by the effect of an increase in the driving force Fout transmitted from the handle 17 to the rotating body 21. Therefore, an appropriate grasping force can be applied to a treatment target even if the end effector 6 is bent, i.e., curved.

First Modification of Second Embodiment

Figure 10A:
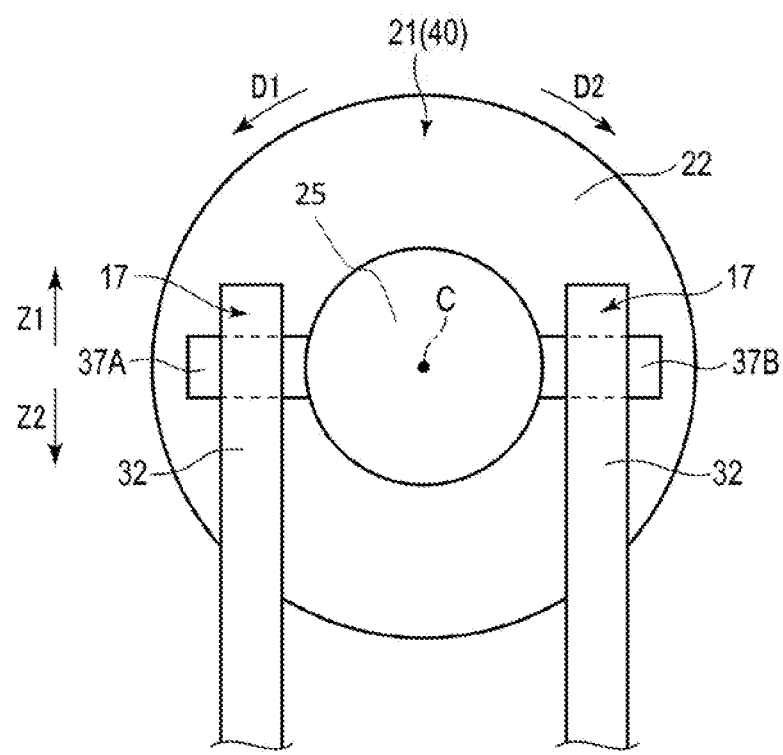
FIG. 10A is a schematic view of a rotor as viewed from a proximal end side when an end effector in a first modification of the second embodiment is in a neutral state.
Figure 10B:
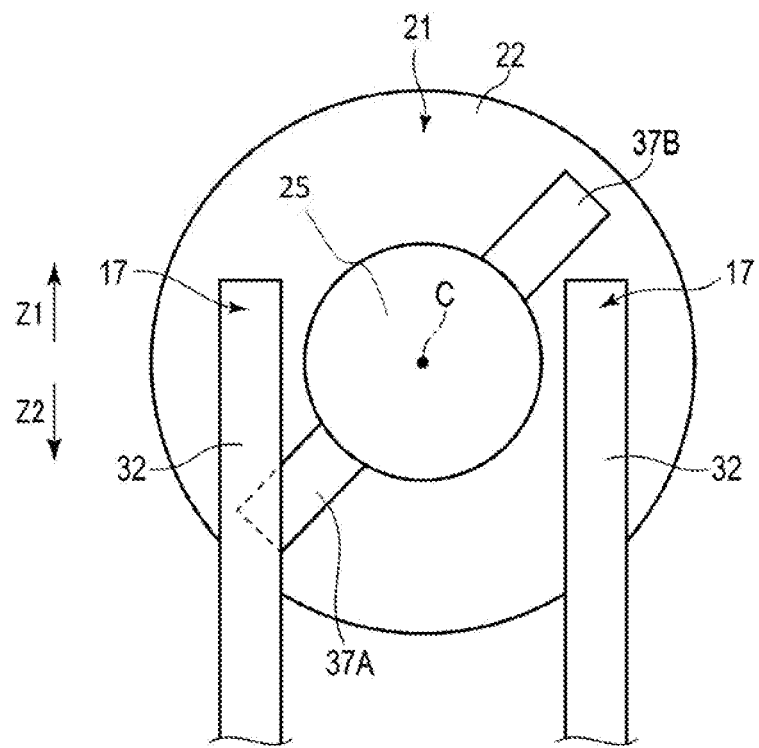
FIG. 10B is a schematic view of the rotor as viewed from the proximal end side when the end effector has been bent relative to a shaft in the first modification of the second embodiment.
Figure 11:
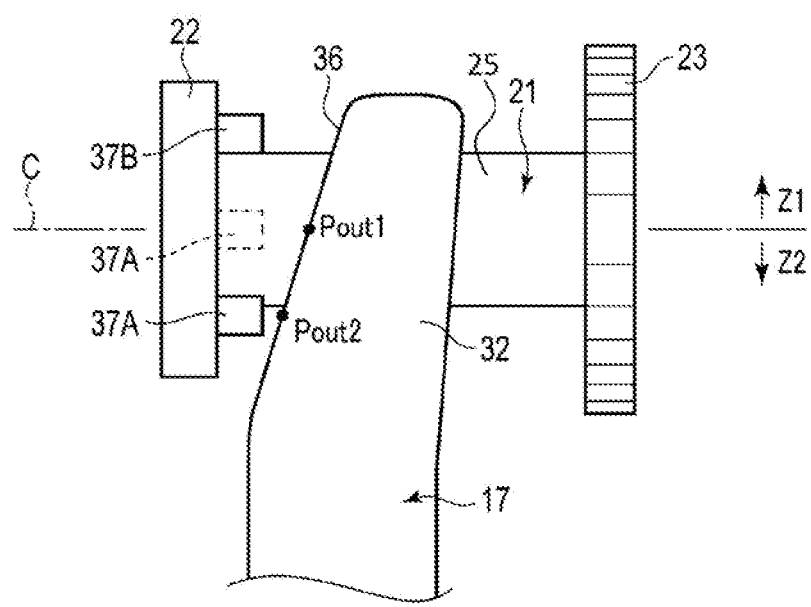
FIG. 11 is a view schematically illustrating a correlation between protrusions and a handle in the first modification of the second embodiment.

FIGS. 10A to 11 are views illustrating a first modification of this embodiment. An end effector 6 of this modification can be bent to both sides (the side indicated by arrow B1 and the side indicated by arrow B2) in a bending direction from the neutral state that the bent angle to the shaft 5 is 0°.

In this modification, the rotating body 21 includes two protrusions 37A and 37B. The protrusions 37A and 37B are each disposed on the groove portion 25 at a position near the flange portion 22, and are each located between the flange portion 22 and the engagement portion 32 of the handle 17 as viewed in the longitudinal direction. The protrusions 37A and 37B are disposed on opposite sides to each other about the longitudinal axis C with the longitudinal axis C being interposed therebetween.

As illustrated in FIG. 11, the distal end face 36 of the engagement portion 32 of the handle 17 is formed in a state in which, with the distal end face 36 of the engagement portion 32 of the handle 17 being in contact with the protrusion 37A or 37B from the proximal end side, the distal end face 36 separates more from the flange portion 22 as the distance from the fulcrum position T (see FIGS. 2A and 2B) increases.

When the end effector 6 is in the neutral state, for example, the protrusions 37A and 37B are located on opposite sides with respect to the longitudinal axis C as viewed in the width direction of the housing 4 and are located on substantially the same position relative to each other in the extending direction of the grip 16, as illustrated by broken lines in FIGS. 10A and 11. In this case, by inputting an operation at the handle 17, the engagement portion 32 of the handle 17 comes into contact with both of the protrusions 37 and 38. Therefore, the contact position between the handle 17 and the protrusion 37A and the contact position between the handle 17 and the protrusion 37B are both used as a first acting position Pout1. At this time, the length between the first acting position Pout1, i.e., first contact position, and the fulcrum position T has a first value b1. At this time, the transmission ratio H has a first value H1, and the leverage K has a first value K1. To the rotating body 21 and the movable shaft 15, a first driving force Fout1 is transmitted from the handle 17 via the protrusions 37A and 37B.

By rotation of the rotating body 21 from the state illustrated in FIG. 10A in one of the directions of rotation, for example, in a direction indicated by arrow D1 in FIG. 10A, about the longitudinal axis C, the end effector 6 is bent in one of the bending directions, for example, in the direction indicated by arrow B1 in FIG. 9, relative to the shaft 5. At this time, the positions, i.e., angular positions, of the protrusions 37A and 37B change about the longitudinal axis C as illustrated by solid lines in FIGS. 10B and 11. In addition, the protrusions 37A and 37B move to opposite sides to each other with respect to the longitudinal axis C as viewed in the extending direction of the grip 16. For example, the protrusion 37A moves from the position in the neutral state as illustrated in FIG. 10A to one of opposite sides of the longitudinal axis C (to a side indicated by arrow Z2 in FIG. 10A) as viewed in the extending direction of the grip 16, while the protrusion 37B moves from the position in the neutral state as illustrated in FIG. 10A to the other side of the longitudinal axis C (to a side indicated by arrow Z1 in FIG. 10A) as viewed in the extending direction of the grip 16. Therefore, the protrusions 37A and 37B move to different positions from each other as viewed in the extending direction of the grip 16.

With the protrusions 37A and 37B disposed at different positions from each other as viewed in the extending direction of the grip 16, the engagement portion 32 of the handle 17 can come into contact with only one of the protrusions 37A and 37B. In this case, when an operation is inputted at the handle 17, the engagement portion 32 of the handle 17 comes into contact with only the protrusion 37A from the proximal end side. Therefore, the contact position between the handle 17 and the protrusion 37A is used as a second acting position Pout2. Further, the length between the second acting position Pout2, i.e., the second contact position, and the fulcrum position T has a second value b2 smaller than the first value b1. At this time, the transmission ratio H has a second value H2 greater than the first value H1, and the leverage K has a second value K2 greater than the first value K1. To the rotating body 21 and the movable shaft 15, a second driving force Fout2 greater than the first driving force Fout1 is transmitted from the handle 17 via the protrusion 37A.

By rotation of the rotating body 21 from the state illustrated in FIG. 10A in the other direction of rotation (for example, in a direction indicated by arrow D2 in FIG. 10A) about the longitudinal axis C, the end effector 6 is bent in the other bending direction (for example, in the direction indicated by arrow B2 in FIG. 9) relative to the shaft 5. At this time, the protrusion 37A moves from the position in the neutral state as illustrated in FIG. 10A to one of sides of the longitudinal axis C (to the side indicated by arrow Z1 in FIG. 10A) as viewed in the extending direction of the grip 16, while the protrusion 37B moves from the position in the neutral state as illustrated in FIG. 10A to the other side of the longitudinal axis C (to the side indicated by arrow Z2 in FIG. 10A) as viewed in the extending direction of the grip 16. In this case, the engagement portion 32 of the handle 17 comes into contact with only the protrusion 37B from the proximal end side. Therefore, the contact position between the handle 17 and the protrusion 37B is used as the second acting position Pout2. Further, the length between the second acting position Pout2, i.e., the second contact position, and the fulcrum position T has the second value b2 smaller than the first value b1. At this time, the transmission ratio H has the second value H2 greater than the first value H1, and the leverage K has the second value K2 greater than the first value K1. To the rotating body 21 and the movable shaft 15, the second driving force Fout2 greater than the first driving force Fout1 is transmitted from the handle 17 via the protrusion 37B.

If the rotating body 21 rotates in one of the rotational directions and the end effector 6 is bent in one of the bending directions as described hereinbefore, one of the paired protrusions 37A and 37B forms the acting position Pout of the driving force Fout. If the rotating body 21 rotates in the other rotational direction and the end effector 6 is bent in the other bending direction, the other one of the paired protrusions 37A and 37B forms the acting position Pout of the driving force Fout.

In whichever bending direction the end effector 6 is bent, the distance b between the acting position Pout and the fulcrum position T decreases and the transmission ratio H, the leverage K, and the driving force Fout transmitted from the handle 17 to the rotating body 21 and the movable shaft 15 increase, compared with the case that the end effector 6 is in the neutral position, in this modification as described hereinbefore. In whichever direction the end effector 6 is bent, the effect of a decrease in the transmission efficiency of the axial force from the movable shaft 15 to the end effector 6 by bending or curving of the end effector 6 is hence canceled by the effect of an increase in the driving force Fout transmitted from the handle 17 to the rotating body 21 and the movable shaft 15.

Third Embodiment

Figure 12:
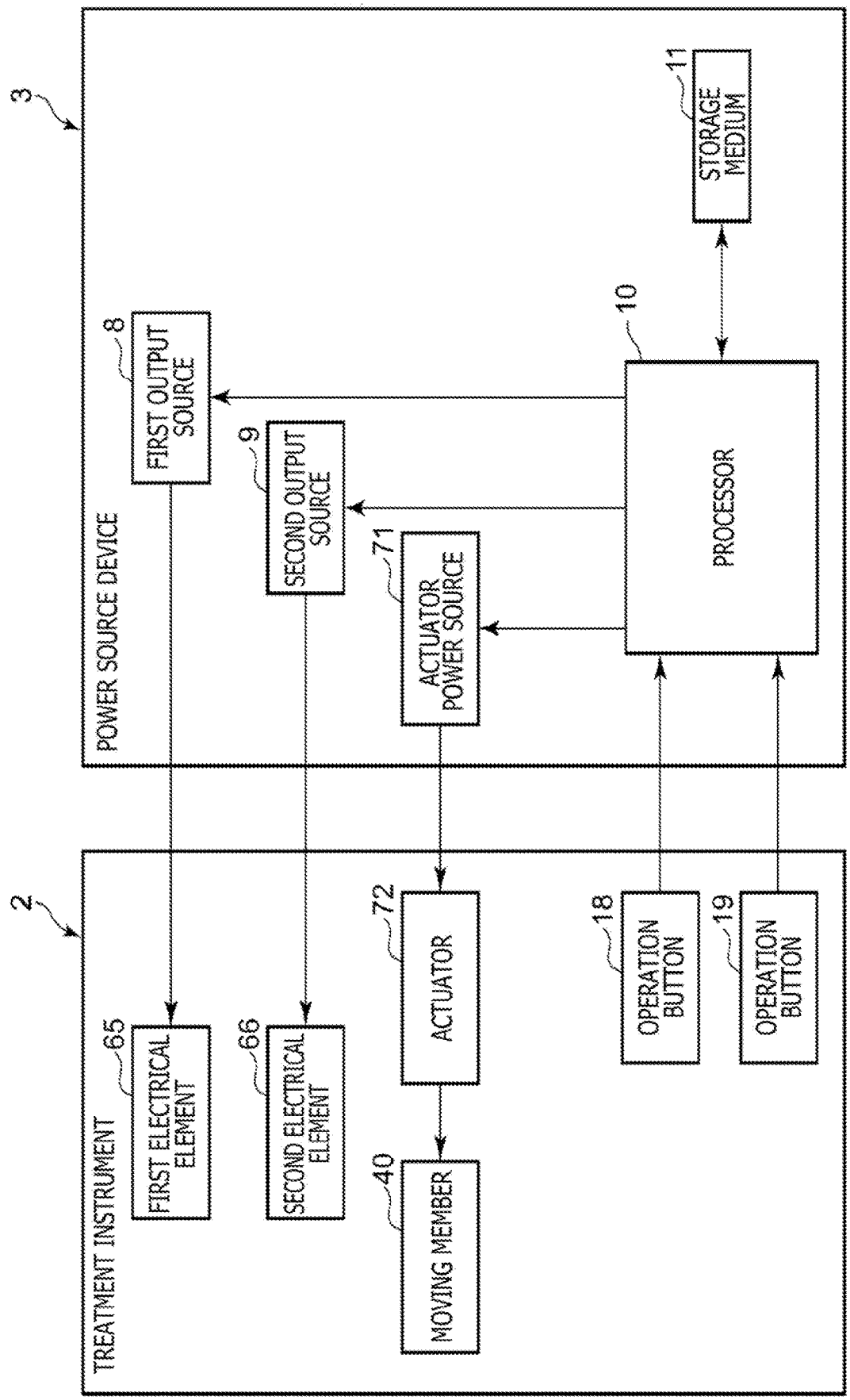
FIG. 12 is a block diagram schematically illustrating a configuration that supplies electrical energy to a treatment instrument according to a third embodiment.

With reference to FIG. 12, a description will be made about a third embodiment of the disclosed technology. The third embodiment is similar in configuration to the first embodiment except for modifications to be described hereinafter. The same elements as in the first embodiment are identified by the same numeral references, and their description is omitted.

FIG. 12 is a diagram illustrating a configuration to supply electrical energy to a treatment instrument 2. As illustrated in FIG. 12, a power source device 3 includes a processor 10 and a storage medium 11. The processor 10 is built from an integrated circuit, a circuitry, and the like, including a CPU (Central Processing Unit), an ASIC (Application Specific Integrated Circuit), an FPGA (Field Programmable Gate Array), or the like. Only one processor 10 may be arranged in the power source device 3, or a plurality of processors 10 may be arranged in the power source device 3. Processing at the processor 10 is performed according to programs stored in the processor 10 or the storage medium 11. In the storage medium 11, processing programs which are to be used at the processor 10, and parameters, functions, tables, and like which are to be used in arithmetic and logic operations at the processor 10 are also stored. The processor 10 detects operation inputs at the operation buttons 18 and 19.

The treatment instrument 2 includes at least one electrical element, i.e., electrical device. In this embodiment, the treatment instrument 2 includes a first electrical element 65 and a second electrical element 66. On the other hand, the power source device 3 includes a first output source 8 and a second output source 9. The first output source 8 includes a conversion circuitry or the like and converts electrical power, which has been supplied from a battery power source, a commercial power outlet, or the like, to electrical energy to be supplied to the first electrical element 65. The first output source 8 then outputs the converted electrical energy to the first electrical element 65. On the other hand, the second output source 9 includes a conversion circuitry or the like and converts electrical power, which has been supplied from the battery power source, a commercial power outlet, or the like, to electrical energy to be supplied to the second electrical element 66. The second output source 9 then outputs the converted electrical energy to the second electrical element 66. The electrical elements 65 and 66 are each activated when supplied with electrical energy. When activated, the electrical elements 65 and 66 can apply treatment energy to a treatment target grasped between the grasping jaws 13 and 14.

In an example, a bipolar electrode is arranged as the first electrical element 65 in the end effector 6, and high-frequency electrical power is outputted from the first power source 8 to the bipolar electrode. By the supply of the high-frequency electrical power to the bipolar electrode with a treatment target grasped between the grasping jaws 13 and 14, a high-frequency current flows through the treatment target between driven electrodes and is applied as treatment energy to the treatment target. With heat caused by the high-frequency current, the treatment target is denatured, sealed, or incised.

As the second electrical element 66, on the other hand, a heater is arranged in the end effector 6, and DC (Direct-Current) power or AC (Alternating-Current) power is outputted as electrical energy from the second output source 9 to the heater. By the supply of the DC power or AC power to the heater, heat is generated from the heater. With a treatment target grasped between the grasping jaws 13 and 14, heat is generated from the heater, whereby the heat from the heater is applied as treatment energy to the treatment target. With the heat from the heater, the treatment target is sealed or incised.

In another example, an ultrasonic transducer is arranged, instead of the heater, as the second electrical element 66 inside the housing 4. The ultrasonic transducer is connected to a rod member (not illustrated) that forms one of the grasping jaws 13 and 14. AC power of a frequency in a predetermined frequency range is then outputted as electrical energy from the second output source 9 to the ultrasonic transducer. By the supply of the AC power to the ultrasonic transducer, ultrasonic vibrations are generated and transmitted to the one grasping jaw 13 or 14 via the rod member. By the transmission of the ultrasonic vibrations to the one grasping jaw 13 or 14 with a treatment target grasped between the grasping jaws 13 and 14, the ultrasonic vibrations are applied as treatment energy to the treatment target. The treatment target is sealed or incised with frictional heat caused by the ultrasonic vibrations.

When an operation input, i.e., first operation input, is performed at the operation button 18, i.e., first operation member, electrical continuity is established between electrical contacts arranged inside the housing 4, whereby an electrical signal is sent to the processor 10 to indicate the performance of the operation input at the operation button 18. When an operation input, i.e., second operation input, is performed at the operation button 19, i.e., second operation member, on the other hand, electrical continuity is established between electrical contacts arranged inside the housing 4, whereby an electrical signal is sent to the processor 10 to indicate the performance of the operation input at the operation button 19.

The processor 10 controls the output of electrical energy from the output source 8 or 9 based on the operation at the operation button 18 or 19, and controls the supply of electrical energy to the electrical element 65 or 66. As a consequence, the application of treatment energy such as a high-frequency current, ultrasonic vibrations, or heat from the heater to the treatment target is controlled. At least one kind of treatment energy such as a high-frequency current, ultrasonic vibrations, or heat from the heater is hence applied to the treatment target.

If an operation input is performed at the operation button 18, the processor 10 performs control to supply electrical energy to the treatment instrument 2 in a first supply mode. If an operation input is performed at the operation button 19, on the other hand, the processor 10 performs control to supply electrical energy to the treatment instrument 2 in a second supply mode different from the first supply mode.

Further, an actuator 72 such as an electric motor or a solenoid is arranged in the treatment instrument 2. The actuator 72 is arranged, for example, inside the housing 4. In addition, an actuator power source 71 is arranged in the power source device 3. The actuator power source 71 includes a conversion circuitry or the like and converts electrical power, which has been supplied from a battery power source, a commercial power outlet, or the like, to electrical energy to be supplied to the actuator 72. By the supply of the electrical energy to the actuator 72, the actuator 72 is operated to generate a driving force for driving the moving member 40.

Based on the operation input at the operation button 18 or 19, the processor 10 controls an output from the actuator power source 71 to control the operation of the actuator 72. Through the control of the operation of the actuator 72 by the processor 10, the driven state of the moving member 40 is controlled. The contact position, i.e., acting position Pout, between the handle 17 and the moving member 40, the distance b between the fulcrum position T of the handle 17 and the acting position Pout, the transmission ration H, and the leverage K are therefore adjusted by the processor 10 based on the operation inputs at the operation buttons 18 and 19.

If an operation input is performed at the operation button 18, i.e., first operation member, for example, the processor 10 controls the driven state of the moving member 40 such that the distance b between the fulcrum position T and the acting position Pout has the first value b1. At this time, the transmission ratio H has the first value H1, and the leverage K has the first value K1. Further, a first driving force Fout1 acts from the handle 17 to the moving member 40. The processor 10 then performs control to supply electrical energy to the electrical element 65 in the first supply mode to apply treatment energy to the treatment target.

If an operation input is performed at the operation button 19, i.e., second operation member, on the other hand, the processor 10 controls the driven state of the moving member 40 such that the distance b between the fulcrum position T and the acting position Pout has the second value b2 smaller than the first value b1. At this time, the transmission ratio H has the second value H2 greater than the first value H1, and the leverage K has the second value K2 greater than the first value K1. A second driving force Fout2 greater than the first driving force Fout1 is transmitted from the handle 17 to the moving member 40. The processor 10 then performs control to supply electrical energy to the electrical element 66 in the second supply mode to apply treatment energy to the treatment target.

In a further example, a bipolar electrode is arranged as the first electrical element 65, and a heater is arranged as the second electrical element 66. In a first supply mode, electrical energy is supplied to the bipolar electrode only. When electrical energy is supplied to the treatment instrument 2 in the first supply mode with a treatment target grasped between the grasping jaws 13 and 14, only a high-frequency current is therefore applied to the treatment target. As a consequence, treatment is performed to seal or solidify the treatment target. In a second supply mode, on the other hand, electrical energy is supplied to both the bipolar electrode and the heater. When electrical energy is supplied to the treatment instrument 2 in the second supply mode with a treatment target grasped between the grasping jaws 13 and 14, both a high-frequency current and heat from the heater are therefore applied to the treatment target at the same time. As a consequence, treatment is performed to seal or solidify the treatment target and at the same time, to incise the treatment target.

If heat generated at the heater is used as treatment energy, it is preferred to apply a large grasping force to a treatment target in treatment that incises the treatment target. In treatment that seals a treatment target, on the other hand, no large grasping force can be applied to the treatment target for the prevention of incision of the treatment target. In the second supply mode for performing incision of the treatment target, the second driving force Fout2 greater than the first driving force Fout1 in the first supply mode for performing sealing of the treatment target is transmitted to the moving member 40 and the movable shaft 15. Therefore, a grasping force greater than that for sealing treatment can be applied to the treatment target in the incision treatment. As a consequence, the performance of treatment is improved in the treatment that uses the treatment instrument 2. As is appreciated from the foregoing, the magnitude of a grasping force to be applied to a treatment target changes according to the treatment, so that an appropriate grasping force conforming to the treatment can be applied to the treatment target.

In a still further example, a bipolar electrode is arranged as the first electrical element 65, and an ultrasonic transducer is arranged as the second electrical element 66. In this embodiment, electrical energy is supplied to both the bipolar electrode and the ultrasonic transducer in a first supply mode. When electrical energy is supplied to the treatment instrument 2 in the first supply mode with a treatment target grasped between the grasping jaws 13 and 14, both a high-frequency current and ultrasonic vibrations are therefore applied to the treatment target at the same time. As a consequence, treatment is performed to seal or solidify the treatment target and at the same time, to incise the treatment target. In this example, electrical energy is supplied only to the bipolar electrode in a second supply mode. When electrical energy is supplied to the treatment instrument 2 in the second supply mode with a treatment target grasped between the grasping jaws 13 and 14, only a high-frequency current is applied to the treatment target. As a consequence, treatment is performed to seal or solidify the treatment target.

In sealing treatment that applies only a high-frequency current to a treatment target, it is preferred to apply a large grasping force to the treatment target. In incision treatment that applies both a high-frequency current and ultrasonic vibrations to a treatment target, on the other hand, no large grasping force can be applied for improvements in the transmissibility of ultrasonic vibrations. In the second supply mode for performing sealing treatment, the second driving force Fout2 greater than the first driving force Fout1 to act on the moving member 40 in the first supply mode for performing incision treatment is transmitted to the moving member 40 and the movable shaft 15. Therefore, a grasping force greater than that for incision treatment can be applied to the treatment target in the sealing treatment. As a consequence, the performance of treatment is improved in the treatment that uses the treatment instrument 2. As is appreciated from the foregoing, the magnitude of a grasping force to be applied to a treatment target changes according to the treatment, so that an appropriate grasping force conforming to the treatment can be applied to the treatment target.

Owing to the control performed as described hereinbefore, the performance of an operation input at one of the plural operation members leads to driving of the moving member 40, so that the acting position Pout, the distance b, the transmission ratio H, and the leverage K are automatically adjusted by the processor 10 to appropriate location and values conforming to the treatment to be performed based on the operation input. Described specifically, the processor 10 automatically adjusts the grasping force between the grasping jaws 13 and 14 to an appropriate magnitude conforming to the treatment to be performed based on the operation input. After the grasping force between the grasping jaws 13 and 14 has been automatically adjusted by the processor 10, electrical energy is supplied to the electrical element 65 and/or the electrical element 66 in the supply mode corresponding to the operation input, whereby treatment energy is applied to the treatment target.

In a yet further example of this embodiment, when an operation input is performed at the operation button 18, a driving force is transmitted to the moving member 40 by a mechanical configuration, and the distance b is adjusted to the first value b1. When an operation input is performed at the operation button 19, on the other hand, a driving force is transmitted to the moving member 40 by a mechanical configuration, and the distance b is adjusted to the second value b2.

Common Configurations Among Embodiments

A medical device 2 includes a sheath, i.e., shaft, disposed extending from a proximal end side toward a distal end side along a longitudinal axis C, a housing 4 connected to a proximal end side of the sheath 5, an end effector 6 including a pair of grasping jaws 13 and 14 openable and closable relative to each other and disposed on a distal end portion of the sheath 5, a movable shaft 15 connected at a distal end thereof to the end effector 6 and configured to be movable relative to the sheath 5 along the longitudinal axis C, whereby the paired grasping jaws 13 and 14 are opened or closed relative to each other, a movable handle 17 configured to be pivotal relative to the housing 4 about a pivot T and having an extension end 38 extending from the housing 4, and a moving member 40 forming an acting position Pout, where a driving force Fout is caused to act from the movable handle 17 to the movable shaft 15 to move the movable shaft 15, and configured to change a ratio K of a first length A from the pivot T to the extension end 38 to a second length b from the pivot T to the acting position Pout of the driving force Fout through a movement relative to the movable handle 17.

The disclosed technology is not limited to the embodiments and modifications described hereinbefore, and various modifications are possible in practice within a scope not departing from the spirit of the disclosed technology. Further, the individual embodiments and modifications may be practiced in combination as much as possible as needed, and in such cases, combined advantageous effects can be brought about. Furthermore, inventions of various levels are included in the embodiments and modifications described hereinbefore, and a variety of inventions can be derived by appropriate combinations of the plural features disclosed herein.

In sum, the disclosed technology is directed to a medical device comprises a housing and an elongated sheath having opposed respective proximal and distal ends extending along a longitudinal axis and being attached from the proximal end to the housing. An end effector is configured to be attached to the distal end portion of the sheath. The end effector includes a pair of grasping jaws capable of be openable and closable with respect to one another. A movable shaft includes a distal end that being connected at to the end effector and configured to be movable with respect to the sheath along the longitudinal axis so as to cause the paired grasping jaws to be opened or closed with respect to one another. A movable handle is configured to pivot with respect to the housing via an axis of pivot and having an input position where an operation is inputted so as to cause the handle to pivot. The movable shaft and the movable handle are configured such that at least one of a first length from the axis of pivot to the input position and a second length from the axis of pivot to an acting position where a driving force acts to move the movable shaft is changeable in an initial state before the operation is inputted at the input position.

The medical device further comprises a moving member configured to change the second length through a movement relative to the movable handle. The moving member is configured to change the acting position where the driving force acts from the movable handle to the movable shaft through a movement relative to the movable handle. The moving member is configured to change the driving force which acts from the movable handle to the movable shaft in magnitude through a movement relative to the movable handle. The moving member includes a rotor that is rotatable relative to the movable handle about the longitudinal axis.

The rotor includes an engagement portion configured to come into contact with the movable handle and to form the acting position of the driving force from the movable handle to the movable shaft. The engagement portion is configured to change in angular position about the longitudinal axis upon rotation of the rotor relative to the movable handle about the longitudinal axis.

The end effector is configured to be bent or curved relative to the sheath upon rotation of the rotor relative to the movable handle. The engagement portion is configured such that the second length has a first value when the end effector has a first bent angle or a second value smaller than the first value when the end effector has a second bent angle greater than the first bent angle. The engagement portion includes a pair of engagement portions disposed on opposite sides to one another with respect to the longitudinal axis. The housing includes a grip extending along a direction that intersects the longitudinal axis. The movable handle is opened from or closed toward the grip when pivoted relative to the housing. The movable handle includes an extending portion that extends to an outside from the housing. The medical device further comprises an elastic member disposed on the movable handle on a side opposite to a side on which the grip is located and between the axis of pivot and the extending portion.

The medical device further comprises an auxiliary handle that is pivotal with respect to the movable handle. The elastic member is disposed between the movable handle and the auxiliary handle. The medical device further comprises a moving member configured to form the acting position where the driving force acts from the movable handle to the movable shaft so as to move the movable shaft and to change the second length through a movement relative to the movable handle. The medical device further comprises a first operation member configured to input an operation to supply electrical energy to the medical device in a first supply mode. A second operation member is configured to supply electrical energy to the medical device in a second supply mode that is different from the first supply mode. The movable shaft and the movable handle are configured such that the second length has a first value based on an input of the operation at the first operation member or the second length has a second value, which is different from the first value, based on an input of the operation at the second operation member.

Another aspect of the disclosed technology is directed to a treatment system comprises a housing and an elongated sheath having opposed respective proximal and distal ends extending along a longitudinal axis and being attached from the proximal end to the housing. An end effector is configured to be attached to the distal end portion of the sheath. The end effector includes a pair of grasping jaws capable of be openable and closable with respect to one another. A movable shaft includes a distal end that being connected at to the end effector and configured to be movable with respect to the sheath along the longitudinal axis so as to cause the paired grasping jaws to be opened or closed with respect to one another. A movable handle is configured to pivot with respect to the housing via an axis of pivot, and having an input position where an operation is inputted so as to cause the handle to pivot. A first operation member is configured to input an operation to supply electrical energy to the medical device in a first supply mode. A second operation member is configured to supply electrical energy to the medical device in a second supply mode that is different from the first supply mode. An actuator is configured to move the moving member relative to the movable handle. A processor is configured to control operation of the actuator such that the moving member is controlled in driven state so as to adjust the second length. The movable shaft and the movable handle are configured such that at least one of a first length from the axis of pivot to the input position and a second length from the axis of pivot to an acting position where a driving force acts to move the movable shaft is changeable in an initial state before the operation is inputted at the input position. The movable shaft and the movable handle are configured such that the second length has a first value based on an input of the operation at the first operation member or the second length has a second value, which is different from the first value, based on an input of the operation at the second operation member.

The processor is configured to adjust the second length to the first value by controlling operation of the actuator based on an input of the operation at the first operation member, or adjust the second length to the second value by controlling operation of the actuator based on an input of the operation at the second operation member.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A medical device comprising:
   a housing;
   a sheath extending along a longitudinal axis;
   an end effector provided distally relative to the sheath, the end effector including a pair of grasping jaws configured to open and close;
   a movable shaft provided in the sheath and connected to the end effector, the movable shaft being configured to move with respect to the sheath along the longitudinal axis so as to operate the pair of grasping jaws;
   a first movable handle configured to pivot with respect to the housing about a pivot axis; and
   a flange connected to the movable shaft,
   wherein:
   the flange is configured to rotate about the longitudinal axis to allow the medical device to operate in one of:
      a first state in which the flange contacts with the first movable handle at a first position, and
      a second state in which the flange contacts with the first movable handle at a second position, and
   in a direction orthogonal to the longitudinal axis, a first distance between the pivot axis and the first position is larger than a second distance between the pivot axis and the second position.

2. The medical device of claim 1, wherein a portion of the flange is exposed from the housing and configured to be moved by a user to allow the medical device to operate in one of the first state and the second state.

3. The medical device of claim 1, wherein the flange is further configured such that an operating force received by the first movable handle in a proximal direction is exerted on the flange as:
   a first driving force at the first position when the medical device is in the first state, or
   a second driving force at the second position when the medical device is in the second state,
   wherein the first driving force is smaller than the second driving force.

4. The medical device of claim 1, wherein:
   the flange comprises a first protrusion protruding in a longitudinal direction of the sheath, and
   the first protrusion is configured to contact with the first movable handle at: (i) the first position when the medical device is in the first state, and (ii) the second position when the medical device is in the second state.

5. The medical device of claim 4, wherein the end effector is configured to be bent relative to the sheath upon rotation of the flange relative to the housing.

6. The medical device of claim 4, wherein the flange further comprises a second protrusion disposed on an opposite side of the flange relative to the first protrusion with respect to the longitudinal axis.

7. The medical device of claim 1, wherein:
the housing comprises a fixed handle, wherein
the first movable handle is configured to open from or close toward the fixed handle.

8. The medical device of claim 7, further comprising:
a second movable handle provided distally relative to the first movable handle, and configured to pivot with respect to the sheath around the pivot axis; and
an elastic member disposed between the first movable handle and the second movable handle and configured to bias the first movable handle toward a proximal direction.

9. The medical device of claim 1, further comprising:
a moving member comprising a protrusion,
wherein the flange contacts with the first movable handle via the protrusion.

10. The medical device of claim 1, further comprising:
an electrode provided on the end effector; and
a first operation button configured to input an operation to supply electrical energy to the electrode in a first supply mode.

11. The medical device of claim 10, further comprising:
a heater provided on the end effector; and
a second operation button configured to input an operation to supply electrical energy to the heater in a second supply mode.

12. The medical device of claim 11, wherein:
in the first supply mode, the medical device operates in the first state, and
in the second supply mode, the medical device operates in the second state.

13. The medical device of claim 1, wherein the flange is provided between the movable handle and the movable shaft, and is configured to move toward a distal direction when the movable handle pivots with respect to the housing about the pivot axis.

14. The medical device of claim 1, wherein the flange is configured to contact with the first movable handle at a third position located between the first position and the second position in the direction orthogonal to the longitudinal axis.

15. The medical device of claim 4, wherein the first protrusion is configured to change in angular position about the longitudinal axis upon rotation of the flange relative to the movable shaft.

16. A treatment system comprising:
the medical device of claim 1; and
an actuator configured to move the flange to allow the medical device to operate in one of the first state and the second state.

17. The treatment system of claim 16, further comprising:
a processor configured to control the actuator to move the flange.

18. The treatment system of claim 17, wherein the processor is configured to control the actuator so as to adjust the flange to contact with the first movable handle at the second position.

19. The treatment system of claim 16, wherein the actuator is configured to rotate the flange about the longitudinal axis.

20. A medical device comprising:
a housing;
a sheath extending along a longitudinal direction;
an end effector provided distally relative to the sheath, the end effector including a pair of grasping jaws configured to open and close;
a movable shaft provided in the sheath and connected to the end effector, the movable shaft being configured to move with respect to the sheath along the longitudinal axis so as to operate the pair of grasping jaws;
a first movable handle configured to pivot with respect to the housing about a pivot axis;
a flange connected to the movable shaft;
a moving member configured to be provided between the first movable handle and the flange, and the moving member comprising a protrusion protruding in the longitudinal direction, and
wherein:
the medical device is configured to operate in one of:
a first state in which the protrusion contacts with the first movable handle at a first position, and
a second state in which the protrusion contacts with the first movable handle at a second position,
in a direction orthogonal to the longitudinal direction, a first distance between the pivot axis and the first position is larger than a second distance between the pivot axis and the second position, and
during a movement between the first state and the second state, the moving member is configured to move in a direction intersecting the longitudinal direction.

* * * * *